United States Patent [19]

Aoyama et al.

[11] Patent Number: 5,728,902
[45] Date of Patent: Mar. 17, 1998

[54] METHOD FOR MANUFACTURING 1,1,1,3,3-PENTAFLUOROPROPENE

[75] Inventors: Hirokazu Aoyama; Akinori Yamamoto; Noriaki Shibata, all of Settsu, Japan

[73] Assignee: Daikin Industries Ltd., Osaka, Japan

[21] Appl. No.: 696,527

[22] Filed: Aug. 14, 1996

[30] Foreign Application Priority Data

Sep. 1, 1995 [JP] Japan .................... 7-248608

[51] Int. Cl.$^6$ .................................. C07C 17/363
[52] U.S. Cl. ........................... 570/136; 570/142
[58] Field of Search ................... 570/136, 142

[56] References Cited

U.S. PATENT DOCUMENTS 5,594,159  1/1997  Jackson et al. .................... 570/142

OTHER PUBLICATIONS

"Syntheses of Fluoroorganic Compounds", I.L. Knunyants and G. G. Yakobson, Springer–Verlag, Berlin Heidelberg, New York, Tokyo, 1985, pp. 8–9.

*Primary Examiner*—C. Warren Ivy
*Assistant Examiner*—Lyman H. Smith
*Attorney, Agent, or Firm*—Armstrong, Westerman, Hattori, McLeland & Naughton

[57] ABSTRACT

A method for manufacturing 1,1,1,3,3-pentafluoropropene comprises the steps of adding 2-trifluoromethyl-3,3,3-trifluoropropionic acid under the presence of metal carbonate and/or metal hydrogencarbonate in an aprotic solvent at reaction temperature particularly from 40° C. to 80° C., of refining resulting reaction products to obtain 1,1,1,3,3-pentafluoropropene, and further of coexisting a desiccating agent therein.

According to the method, 1,1,1,3,3-pentafluoropropene can be manufactured through industrially efficient and cost-effective way using 2-trifluoromethyl-3,3,3-trifluoropropionic acid as a raw material.

8 Claims, No Drawings

METHOD FOR MANUFACTURING 1,1,1,3,3-PENTAFLUOROPROPENE

FIELDS OF INDUSTRIAL APPLICATION

The present invention relates to a method for manufacturing 1,1,1,3,3-pentafluoropropene, which is useful as an intermediate for manufacturing 1,1,1,3,3-pentafluoropropane that can be substitutes for CFC and HCFC as refrigerants, blowing agents and cleaning agents, and which is useful as a macromolecule monomer containing fluorine.

CONVENTIONAL METHODS

There is conventionally known a method of manufacturing 1,1,1,3,3-pentafluoropropene by decarboxylation (a reaction of removing $CO_2$) of neutralized potassium salt of 2-trifluoromethyl-3,3,3-trifluoropropionic acid by the use of potassium hydrogencarbonate (Syntheses of Fluoroorganic Compounds, Knunyants I. L., Yakobuson G. G., Springer-Verlag, 1985, page 8 to 9).

This conventional method in the above-stated literature, however, has difficulty in a large-scale manufacturing because 2-trifluoromethyl-3,3,3-trifluoropropionic acid is reacted in the presence of solid potassium hydrogencarbonate, and in addition to this, it also has difficulty in a large-scale manufacturing because of requirement of an operation to remove a lot of water produced in neutralization or desiccating in a vacuum dessicator in the presense of phosphorus pentoxide as a desiccating agent.

Further, in the decarboxylation, potassium salt of 2-trifluoromethyl-3,3,3-trifluoropropionic acid is filled in a reactor to carry out the decarboxylation by heating. In case of an industrial manufacturing of large-scale, it is hard to control an amount of produced carbon dioxide gas and 1,1,1,3,3-pentafluoropropene. To deal with this problem, it is nessesary to install over-scaled apparatus and this leads to disadvantages in the economical aspects of the process.

OBJECTIVE OF THE INVENTION

An objective of the present invention is to provide a method to produce 1,1,1,3,3-pentafluoropropene from 2-trifluoromethyl-3,3,3-trifluoropropionic acid as a raw material through an industrially efficient and cost-effective way.

CONTENTS OF THE INVENTION

The inventors have thoroughly studied industrially efficient and cost-effective production methods of 1,1,1,3,3-pentafluoropropene. As a result, they have discovered that an alkali metal salt of 2-trifluoromethyl-3,3,3-trifluoropropionic acid is produced in the reaction system by reaction of 2-trifluoromethyl-3,3,3-trifuluoropropionic acid with an alkali metal carbonate and/or an alkali metal hydrogencarbonate in an aprotic solvent to react with each other as these reactants are added gradually, further, 1,1,1,3,3-pentafluoropropene is produced at once by decarboxylation proceeding in the reaction system, and the by-product of 1,1,1,3,3,3-hexafluoropropane caused by water produced in neutralization can be suppressed by coexistence of the desiccating agent. The present invention has been accomplished based on this discovery.

That is, the present invention provides a method for manufacturing 1,1,1,3,3-pentafluoropropene which is produced by adding or dropping 2-trifluoromethyl-3,3,3-trifluoropropionic acid under the presence of metal carbonate and/or metal hydrogencarbonate in an aprotic solvent at a reaction temperature particularly from 40° C. to 80° C. and, particularly, 1,1,1,3,3-pentafluoropropene is obtained by refining the resulted reaction products, and preferably by coexisting a desiccating agent.

The reaction in the present invention, using potassium carbonate for an example, is presumed to be proceeded as follows:

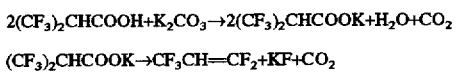

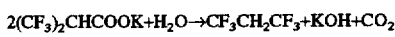

A side-reaction which is caused by the existence of water is described by the following formula. To control this side-reaction, the desiccating agent can be coexisted.

$2(CF_3)_2CHCOOK+H_2O \rightarrow CF_3CH_2CF_3+KOH+CO_2$

As described above, 2-trifluoromethyl-3,3,3-trifluoropotassium-propionate, carbon dioxide and water are produced by the neutralization reaction of 2-trifluoromethyl-3,3,3-trifluoropropionic acid and potassium carbonate. Compared with ordinary alkali metal salt of carboxylic acid, 2-trifluoromethyl-3,3,3-trifluoro-potassium-propionate produced in the reaction system tends to be decarboxylated, and is immediately decarboxylated at a reaction temperature to generate 1,1,1,3,3-pentafluoropropene. Because the water produced in the neutralization is removed by the desiccating agent which exists in the reaction system, progress of the above-described side-reaction can be suppressed.

In the present invention, anhydrous potassium carbonate, anhydrous sodium carbonate, anhydrous potassium hydrogencarbonate, anhydrous sodium hydrogencarbonate and so on can be used as the metal carbonate or metal hydrogencarbonate.

The amount of the metal carbonate or the metal hydrogencarbonate is not particularly limited, but preferably is not less than a stoichiometric amount to 2-trifluoromethyl-3,3,3-trifluoropropionic acid.

The desiccating agent, in the present invention, can be anhydrous calcium chloride, anhydrous magnesium sulfate, anhydrous sodium sulfate, anhydrous calcium sulfate or the like. Because anhydrous potassium carbonate or anhydrous sodium carbonate can be used as the desiccating agent, these compounds can be partially used as the desiccating agent when not less than necessary amount for the reaction is added. Molecular Sieves, silica gel, alumina, active carbon and so on can be used as the desiccating agent.

There is no particular restriction in an amount of the desiccating agent, however, an amount which can sufficiently remove the water produced in the neutralization is preferably used.

The aprotic solvent usable in the present invention can be amides of N,N-dimethylformamide, N,N-dimethylacetamide, N-methylpyrrolidone, hexamethylphosphorictriamide and so on; sulfoxides of dimethyl-sulfoxide, sulfolane and so on; glymes of ethyleneglycol dimethylether, diethyleneglycol dimethylether, triethyleneglycol dimethylether and so on; esters of ethyl acetate, butyl acetate and so on; ketones of acetone, methylethylketone and so on; nitriles of acetonitrile, benzonitrile and so on. The esters such as ethyl acetate and butyl acetate etc. are especially desirable.

There is no problem using a metal carbonate or a metal hydrogen-carbonate without being perfectly dissolved in the solvent. For example, it is also possible to conduct the reaction under a condition that the metal carbonate or the metal hydrogencarbonate is suspended in the solvent.

The reaction temperature can be varied with the kind of the solvent, but it is ordinarily 30° C. to 100° C., preferably 40° C. to 80° C.

2-trifluoromethyl-3,3,3-trifluoropropionic acid as a raw material can be easily produced by the reaction of perfluoroisobutenylmethylether and calcium chloride in the presence of a mixed solvent of tetrahydrofuran and water, the perfluoroisobutenylmethylether being obtained by the reaction of dehydrofluorination (removing HF) of perfluoroisobutylmethylether (a methanol addition compound of perfluoroisobutene) and potassium hydroxide to cause dehydrofluorination (See Japanese patent application No. 152567/95).

In addition, 1,1,1,3,3-pentafluoropropane can be manufactured by hydrogenation of 1,1,1,3,3-pentafluoropropene as a raw material with hydrogen in the presence of hydrogenation catalyst, the former of which is obtained by the method of the above-stated present invention.

In the hydrogenation, the reaction products which are obtained by the manufacturing method of the above-stated present invention contain 1,1,1,3,3-pentafluoropropene and the remains, for example, carbon dioxide, 1,1,1,3,3,-hexafluoropropane, and the reaction solvent depending on the situation. Since these reaction products have no reverse influence on the succeeding hydrogenation, it is possible to use these reaction products without separating 1,1,1,3,3-pentafluoropropene therefrom. When necessary, it is also possible to refine it to separate from the reaction products before use for the hydrogenation.

The reaction can be conducted in a liquid or gaseous phase at a reaction temperature from −20° C. to 300° C.

The hydrogenation catalyst preferably comprises a noble metal, for example, palladium, platinum, rhodium and so on. Particularly, a palladium catalyst is preferably used.

As a carrier of the catalyst, active carbon, silica gel, titanium oxide, zirconia and so on can be used, preferably active carbon.

INDUSTRIAL APPLICABILITY

The present invention provides a method for manufacturing 1,1,1,3,3-pentafluoropropene which is produced by dropping 2-trifluoromethyl-3,3,3-trifluoropropionic acid under the presence of metal carbonate and/or metal hydrogencarbonate in an aprotic solvent at a specific reaction temperature from 40° C. to 80° C. and, particularly, 1,1,1,3,3-pentafluoropropene is separated by refining from the reaction products which are produced by the above-stated reaction, more preferably produced under coexistence of a desiccating agent. Accordingly, a metal salt of 2-trifluoromethyl-3,3,3-trifluoropropionic acid is produced in the reaction system and decarboxylation is progressed in the reaction system to generate 1,1,1,3,3-pentafluoropropene at once or at one change, and then by-products of 1,1,1,3,3-hexafluoropropane caused by water produced in neutralization can be controled by the presence of the desiccating agent. 1,1,1,3,3-pentafluoropropene thus can be obtained in efficiently in a cost-effective industrial scale.

EMBODIMENTS

The invention will be more specifically explained with reference to the embodiments hereunder.

EMBODIMENT 1

150 ml of ethyl acetate, 34.6 g (0.25 mol) of anhydrous potassium carbonate and 10 g of anhydrous magnesium sulfate were fed into a 300 ml reactor made of glass which was equipped with a dropping funnel and a reflux condenser, and the reactor was heated at 70° C. with stirring of the contents.

With the temperature maintained, 98 g (0.5 mol) of 2-trifluoromethyl-3,3,3-trifluoropropionic acid was dropped from the dropping funnel for 5 hours. Gas having a low boiling point produced during the reaction was taken out from the upper portion of the reflux condenser and trapped in a vessel cooled by dry ice-acetone.

The produced gas having low boiling point in the reaction was analyzed by gas chromatography. As result, it was found that the produced gas contained carbon dioxide, 1,1,1,3,3-pentafluoropropene, 1,1,1,3,3,3-hexafluoropropane and ethyl acetate. Table 1 shows the results of change of the composition of the produced gas, that is, selectivity of the target product according to the time passed from the starting of the dropping of the raw material.

TABLE 1

| Time passed from dropping started (Hour(s)) | Selectivity of 1,1,1,3,3-pentafluoropropene* (%) |
|---|---|
| 2 | 95 |
| 3 | 90 |
| 5 | 82 |

*Selectivity: selectivity of target product gas except carbon dioxide and ethyl acetate After the reaction was completed, the trapped gas was analyzed by gas chromatography. Selectivity of 1,1,1,3,3-pentafluoropropene was 87%.

EMBODIMENT 2

150 ml of ethyl acetate and 50 g (0.36 mol) of anhydrous potassium carbonate were fed into the reactor used in Embodiment 1, and the reactor was heated at 70° C. with stirring of the contents.

With the temperature maintained, 98 g (0.5 mol) of 2-trifluoromethyl-3,3,3-trifluoropropionic acid was dropped from the dropping funnel for 5 hours. Gas having a low boiling point produced during the reaction was taken out from the upper portion of the reflux condenser and trapped in the vessel cooled by dry ice-acetone.

After the reaction was completed, the trapped gas was analyzed by gas chromatography. Selectivity of 1,1,1,3,3-pentafluoropropene was 84%.

EMBODIMENT 3

A reaction was carried out in the same manner as Embodiment 1 except that ethyleneglycol dimethylether was used in place of ethyl acetate as the solvent. After the reaction was completed, the trapped gas was analyzed by gas chromatography. Selectivity of 1,1,1,3,3-pentafluoropropene was 86%.

EMBODIMENT 4

A reaction was conducted in the same manner as Embodiment 1 except that acetonitrile was used in place of ethyl acetate as the solvent. After the reaction was completed, the trapped gas was analyzed by gas chromatography. Selectivity of 1,1,1,3,3-pentafluoropropene was 70%.

EMBODIMENT 5

2.3 cc of palladium catalyst carried on active carbon in concentration of 5% by weight was filled into a SUS316 reaction tube of 7 mm inner diameter and 150 mm length and the tube was heated by an electric furnace at 100° C. while nitrogen gas was flowed therethrough. After the temperature reached the predetermined value, 1,1,1,3,3-pentafluoropropene obtained in Embodiment 1 was introduced at a flow rate of 5.5 cc/min with hydrogen at a flow rate of 14.5 cc/min. The reaction temperature was maintained at 100° C.

The produced gas was washed with water, and then analyzed by gas chromatography. Conversion of 1,1,1,3,3-pentafluoropropene was approximately 100% and selectivity of 1,1,1,3,3-pentafluoropropane was 99.5%.

EMBODIMENT 6

Powdered catalyst comprising 3% by weight of Pd carried on 50 g of active carbon was filled into a SUS316 61 autoclave with a stirring device. After this autoclave was vacuumed and cooled at 5° C., 5 Kg of 1,1,1,3,3-pentafluoropropene was introduced and stirring of the contents was started. After the inside temperature was cooled at 3°, hydrogen was introduced into the autoclave at pressure of 4 Kg/cm$^2$G. The inside temperature was raised at 9° C. with the reaction started.

As cooling of the autoclave was continued from the outside in such a condition that the inside temperature did not exceed 15° C., hydrogen was introduced thereinto at pressure of 4 Kg/cm$^2$G to 5Kg/cm$^2$G. The reaction was continued until absorption of hydrogen was terminated.

After the reaction ended, the inside temperature was cooled at 5° C., and hydrogen was purged from the reaction system. The inside temperature was then raised at 30° C. and the reaction products were collected in a trap cooled by dry ice. 5 Kg of the reaction products was collected, and conversion of 1,1,1,3,3-pentafluoropropene was approximately 100% and selectivity of 1,1,1,3,3-pentafluoropropane from 1,1,1,3,3-pentafluoropropene was 99.2%.

We claim:

1. A method for manufacturing 1,1,1,3,3-pentafluoropropene by the reaction of 2-trifluoromethyl-3,3,3-trifluoropropionic acid under the presence of metal carbonate and/or metal hydrogencarbonate in an aprotic solvent and under the presence of a desiccating agent.

2. A method for manufacturing 1,1,1,3,3-pentafluoropropene according to claim 1 wherein anhydrous alkali metal carbonate or anhydrous alkali metal hydrogencarbonate is used as metal carbonate or metal hydrogencarbonate.

3. A method for manufacturing 1,1,1,3,3-pentafluoropropene according to claim 1 wherein at least a stoichiometric amount of metal carbonate and/or metal hydrogencarbonate to an amount of 2-trifluoromethyl-3,3,3-trifluoropropionic acid is used.

4. A method for manufacturing 1,1,1,3,3-pentafluoropropene according to claim 1 wherein anhydrous metal sulfate, anhydrous metal carbonate or anhydrous metal hydrogencarbonate is used as the desiccating agent.

5. A method for manufacturing 1,1,1,3,3-pentafluoropropene according to claim 4 wherein anhydrous alkali metal carbonate or anhydrous alkali metal hydrogencarbonate is used as anhydrous metal carbonate or anhydrous metal hydrogencarbonate.

6. A method for manufacturing 1,1,1,3,3-pentafluoropropene according to claim 1 wherein amides, sulfoxides, glymes, esters, ketones or nitriles is used as the aprotic solvent.

7. A method for manufacturing 1,1,1,3,3-pentafluoropropene according to claim 1 wherein 1,1,1,3,3-pentafluoropropene is obtained by refining the reaction products obtained by adding 2-trifluoromethyl-3,3,3-trifluoropropionic acid.

8. A method for manufacturing 1,1,1,3,3-pentafluoropropene according to claim 1 wherein the reaction is conducted at 30° C. to 100° C.

* * * * *